United States Patent [19]

Strobl, Jr.

[11] Patent Number: 5,433,605
[45] Date of Patent: Jul. 18, 1995

[54] ADJUSTABLE, DISPOSABLE DENTAL PROPHY TOOL

[76] Inventor: Frederick P. Strobl, Jr., 204 N. Shore Dr., Cary, Ill. 60013

[21] Appl. No.: 123,554

[22] Filed: Sep. 20, 1993

[51] Int. Cl.⁶ ............................ A61C 1/18; A61C 1/12
[52] U.S. Cl. .................................... 433/112; 433/125; 433/126; 433/130
[58] Field of Search ................ 433/112, 125, 126, 130

[56] References Cited

U.S. PATENT DOCUMENTS

| 606,755 | 7/1898 | Browne | 433/112 |
|---|---|---|---|
| 1,678,096 | 7/1928 | Andresen | 433/130 |
| 1,688,136 | 10/1928 | Chayes et al. | 433/130 |
| 1,855,970 | 4/1932 | Kaltenbach et al. | 433/130 |
| 1,875,559 | 9/1932 | Brumm | 433/112 |
| 1,984,663 | 12/1934 | Tatham | 433/130 |
| 2,033,662 | 3/1936 | Witt | 433/130 |
| 3,509,629 | 5/1970 | Kidokoro et al. | 433/130 |
| 3,727,312 | 4/1973 | Durante | 433/130 |
| 5,020,994 | 6/1991 | Huang | 433/126 |

FOREIGN PATENT DOCUMENTS

| 888449 | 12/1943 | France | 433/126 |
|---|---|---|---|
| 3122061 | 2/1982 | Germany | 433/126 |

Primary Examiner—Cary E. O'Connor
Attorney, Agent, or Firm—Staas & Halsey

[57] ABSTRACT

An adjustable, disposable dental prophy tool includes an elongated cylindrical grip end body component and an elongated cylindrical cup end body component. The cup end body component is mounted on the grip end body component so that their major longitudinal axes are offset in non-parallel alignment. A housing for a cleaning and polishing cup drive element is mounted at the outer end of the cup end body component. A drive element is mounted in the housing for rotation about an axis which extends laterally of the longitudinal axis of the elongated cup end body component. The cup end body component is fully rotatable for 360° about its own longitudinal axis relative to the grip end body component. The tool also includes axial locking structure holding the body components together to prevent relative axial movement thereof. The tool also includes releasable angular locking structure selectively inhibiting relative rotation of the body components.

28 Claims, 6 Drawing Sheets

ADJUSTABLE, DISPOSABLE DENTAL PROPHY TOOL

BACKGROUND OF THE INVENTION

1. Field of the Invention

The present invention relates to dental hand tools and particularly to dental prophy tools utilized for cleaning and polishing teeth.

2. Prior Practices in the Art

In the past, dental prophy tools have generally been straight, non-adjustable and non-disposable. Particularly in the health conscious atmosphere existing today, metal, non-disposable dental tools present actual as well as political problems because of the need for prevention of cross-contamination and the need for cleaning, lubricating and sterilizing procedures to eliminate health risks and maintain the tools in proper working condition. But the non-adjustable, non-disposable tools used in the past inhibit teeth cleaning operations because of the difficulty in reaching all areas of the mouth when using such tools. Thus, prior art devices suffer from both a lack of performance capability and the fact that such devices need to be cleaned and maintained.

SUMMARY OF THE INVENTION

The present invention relieves the prior art difficulties discussed above and provides a solution for the same. The invention provides an adjustable, disposable dental prophy tool having a rotatable cup mounting body component which provides greater accessibility to hard-to-reach areas. As a result, the user can clean and polish teeth faster, easier and more thoroughly than ever before. The cup mounting body component may also be angularly disposed relative to the remainder of the tool. Thus, unlike prior art prophy tools, the prophy tool of the present invention provides a unique design facilitating an adjustable contra-angle capable of rotating a full 360°, thereby allowing unlimited maneuverability and flexibility. Moreover, the dental prophy tool of the present invention is molded from inexpensive plastic and is therefore disposable so as to eliminate the risk of cross-contamination as well as the time-consuming need for cleaning, lubricating and sterilizing procedures which were normally required with prior art reusable metal prophy tools.

The problems extant in the prior art are relieved and minimized through the provision, in accordance with the present invention, of an adjustable, disposable, molded plastic dental prophy tool. The tool of the present invention comprises an elongated grip end body component having first and second longitudinally spaced opposite ends. The tool of the invention also includes an elongated cup end body component having a longitudinally extending axis and third and fourth longitudinally spaced opposite ends. The third end of the cup end body component is mounted on the grip end body component at the second end of the latter. The cup end body component is fully rotatable for 360° about its own longitudinal axis relative to the grip end body component. The tool of the present invention also includes a teeth cleaning cup drive element which extends laterally outwardly from the fourth end of the cup end body component. The cup drive element is mounted on the cup end body component for rotation about a drive axis which extends laterally of the longitudinal axis of the cup end body component.

In one form of the invention, the longitudinally extending axis of the cup end body component may be angularly disposed relative to the longitudinal axis of the grip end body component. Moreover, the axes of the body component may cross and such axes may be inclined at an angle of approximately 8° to 12° relative to one another.

The prophy tool of the invention also includes a rotatable driving component which is drivingly connected to the cup drive element for rotating the latter about the drive axis. The driving component may preferably include an elongated, rotatable, flexible driving shaft which extends longitudinally of both the grip end body component and the cup end body component along the axes thereof.

The cup drive element may include a driven gear and an elongated cup drive shaft which extends along the drive axis. The driven gear and the cup drive shaft may be coupled together for rotation together about the drive axis. Correspondingly, the driving component may include a driving gear coupled with the driving shaft for rotation therewith about the longitudinal axis of the driving shaft. The gears are intermeshed for rotation together upon rotation of the flexible driving shaft by an outside motive force.

The disposable dental prophy tool of the present invention may also include axial locking structure preventing relative axial movement of the cup end body component and the grip end body component in a direction along the longitudinal axis of the cup end body component. Preferably, the axial locking structure may include an annular groove in one of the components and a complementary mating annular rib carried by the other of the components. Such rib and such groove may each be positioned concentrically relative to the axis of the cup end body component with the rib being configured for complementary mating with the groove so as to permit relative rotation of the body component while inhibiting relative axial displacement thereof.

The tool may also include releasable angular locking structure selectively inhibiting the rotation of the cup end body component relative to the grip end body component. Such locking structure may preferably include an elongated notch in one of the components and a complementary mating elongated ridge carried by the other of the components. Such notch and such ridge generally may each extend in parallelism relative to the longitudinal axis of the cup end body component, and the notch and the rib are complementarily configured for cooperation so as to inhibit the relative rotation of the body components when the ridge is disposed in the notch.

The gears may preferably be a drive gear and a driven pinion gear which are configured and arranged so as to hold the cup drive element in its operating position when the gears are intermeshed. Moreover, the tool may preferably include interengageable shaft positioning elements on the grip end body component and on the driving component maintaining the driving component in its operating position when the cup end body component is mounted on the grip end body component.

DETAILED DESCRIPTION OF THE INVENTION

Figure 1:
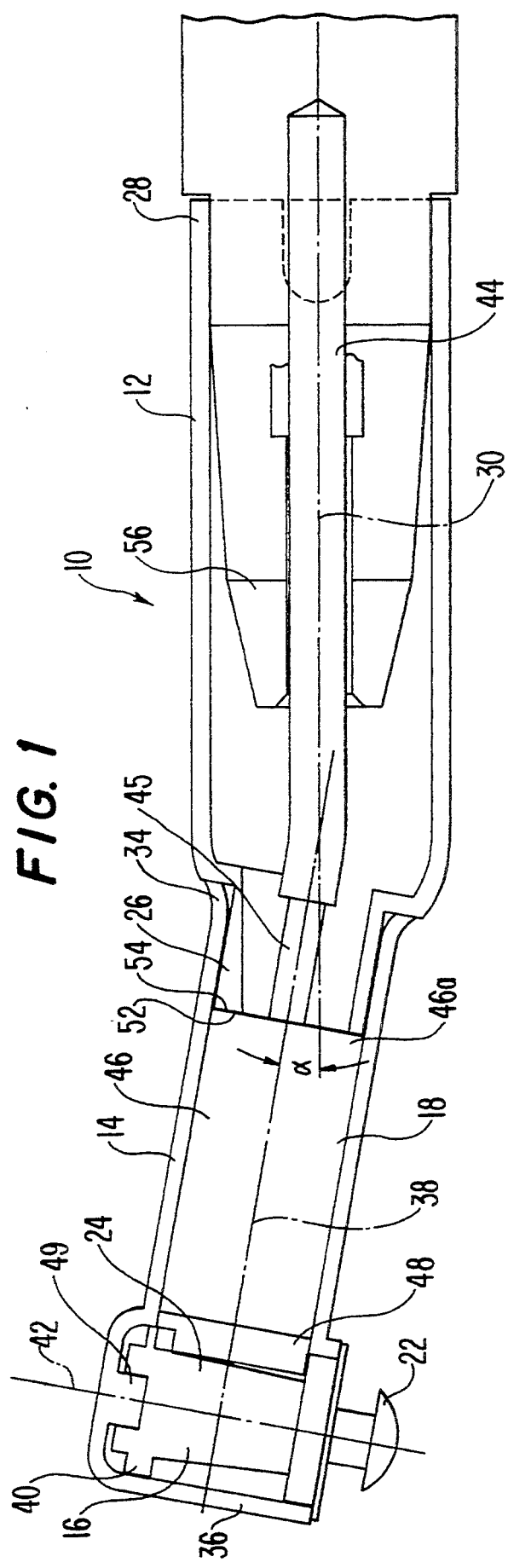
FIG. 1 is a cross-sectional side elevational view of an adjustable, disposable dental prophy tool constructed in accordance with the invention.
Figure 2:
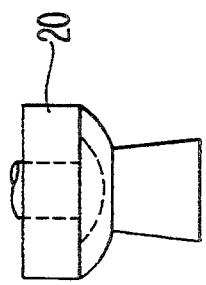
FIG. 2 is a partial side elevational view illustrating the manner in which a teeth cleaning cup is mounted on the tool of FIG. 1.

An adjustable, disposable dental prophy tool constructed in accordance with the present invention is illustrated in FIG. 1 where the tool is identified by the reference numeral 10. The prophy tool 10 is particularly useful for cleaning and polishing teeth.

Figure 4:
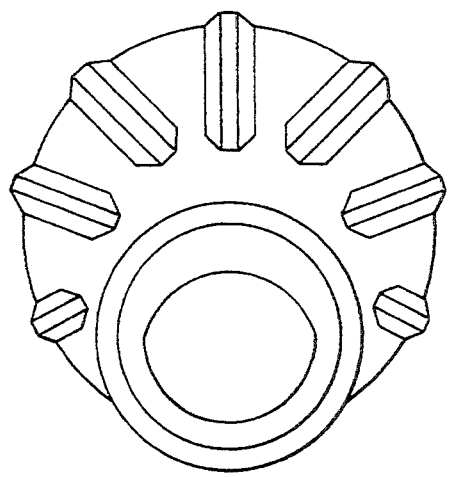
FIG. 4 is an auxiliary view taken along the line 4—4 of FIG. 3.
Figure 5:
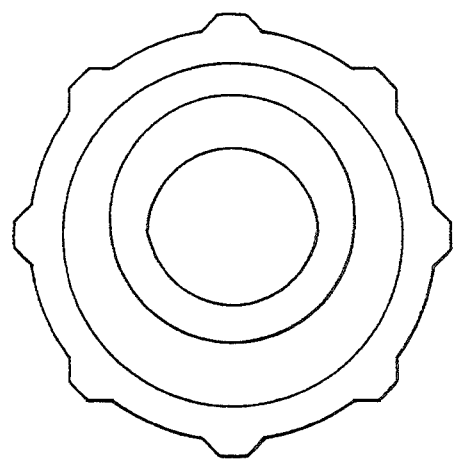
FIG. 5 is a right end elevational view taken along the line 5—5 of FIG. 3.
Figure 14:
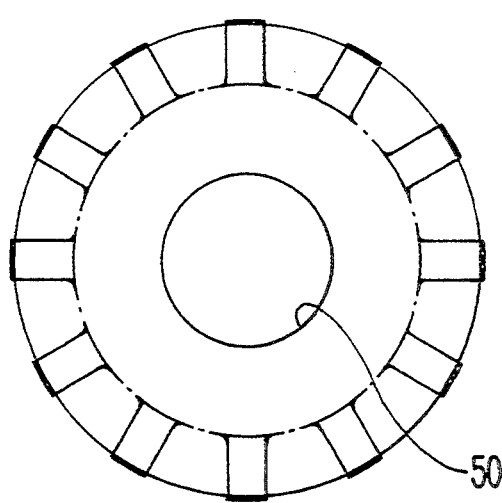
FIG. 14 is an end view taken along the line 14—14 of FIG. 12.
Figure 8:
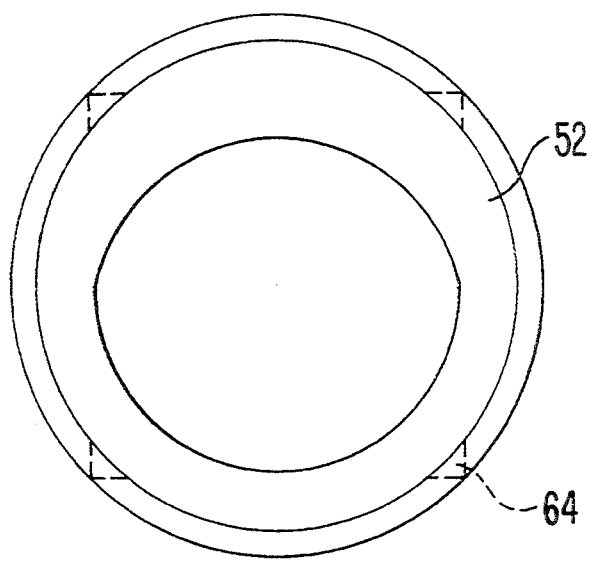
FIG. 8 is an auxiliary view taken along the line 8—8 of FIG. 3.
Figure 11:
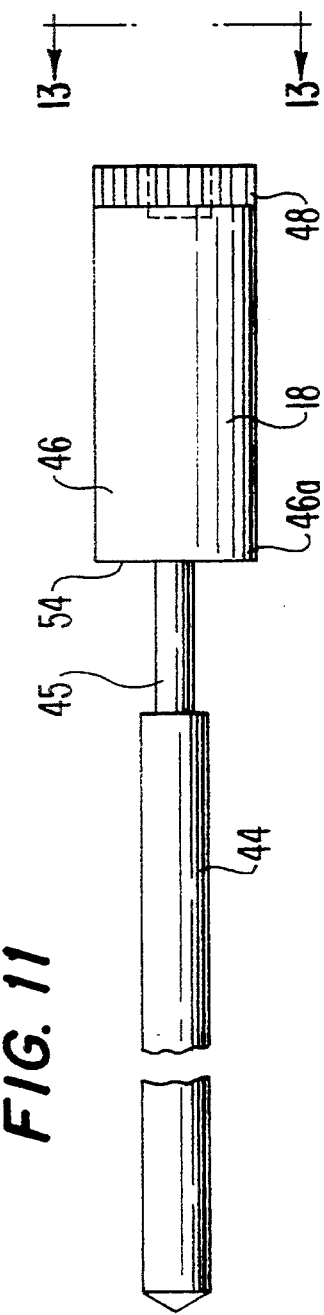
FIG. 11 is an elevational view illustrating the rotatable driving component of the tool of FIG. 1.
Figure 13:
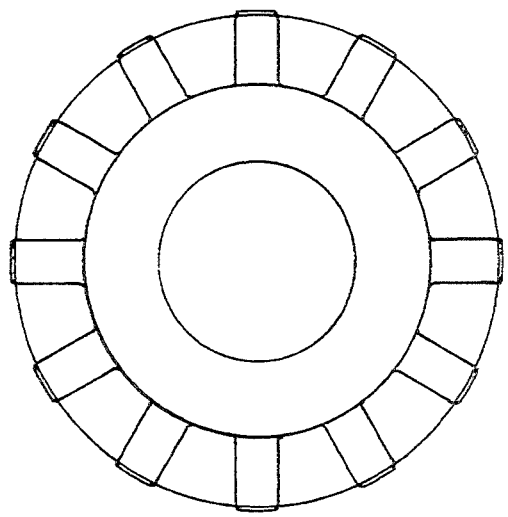
FIG. 13 is an end view taken along the line 13—13 of FIG. 11.

Tool 10 includes a grip end body component 12, a cup end body component 14, a rotatable cup drive element 16 and a rotatable driving component 18. The grip end body component 12 is illustrated in greater detail in FIGS. 3, 4 and 5, the cup end component is illustrated in greater detail in FIGS. 6 and 7, the cup drive element is illustrated in greater detail in FIGS. 12 and 14 and the driving component 18 is illustrated in greater detail in FIGS. 11 and 13.

The major purpose of the tool 10 of the invention is to rapidly rotate a natural rubber teeth cleaning and polishing cup 20 configured to slip over a button 22 carried at the outer end of a drive shaft 24 of element 16. The cup 20 preferably has a pocket configured to slip over button 22 so that the cup 20 and the button 22 are held together by frictional engagement as is well known in the art. In this regard, the cup 20 may be "firm" so as to be effective for polishing amalgam and removing stains. On the other hand, the cup 20 may be "soft" so as to be pliant for fast thorough subgingival and interproximal cleaning. These natural rubber cups are well known in the art and further description thereof is not required at this point. Suffice it to say that the cups are rotated at high speed to facilitate the teeth cleaning and polishing operation.

Figure 3:
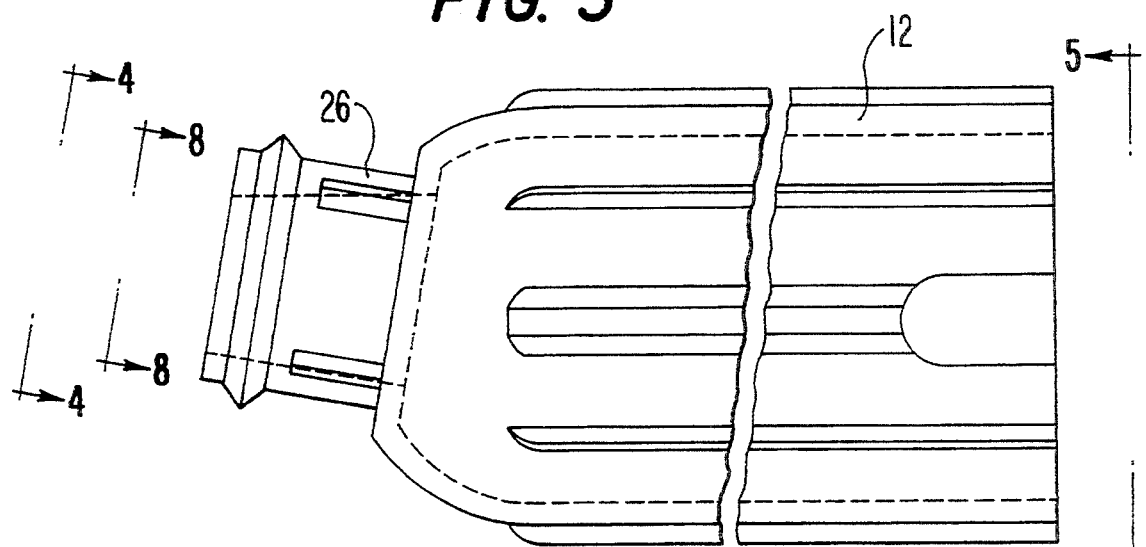
FIG. 3 is an enlarged side elevational view of a grip end body component of the tool of FIG. 1.

Body component 12 is generally cylindrical, and with reference to FIG. 3, it can be seen that body component 12 includes an angularly disposed end portion 26. In this regard, it should be noted that the end portion 26 is shown only schematically in FIG. 1, with the details thereof being more clearly illustrated in FIGS. 3, 4, 8 and 10. Body component 12 also has a tubular end portion 28 at the opposite end thereof, and as can be seen viewing FIG. 1, the end portions 26 and 28 are spaced apart longitudinally of component 12 along the longitudinal axis 30 thereof.

Figure 6:
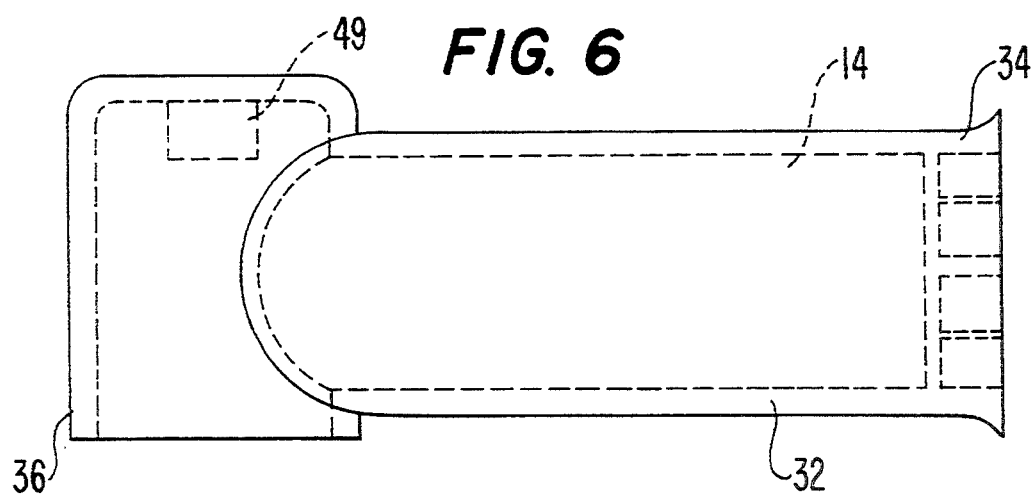
FIG. 6 is an elevational view of the cup end body component of the tool of FIG. 1.
Figure 7:
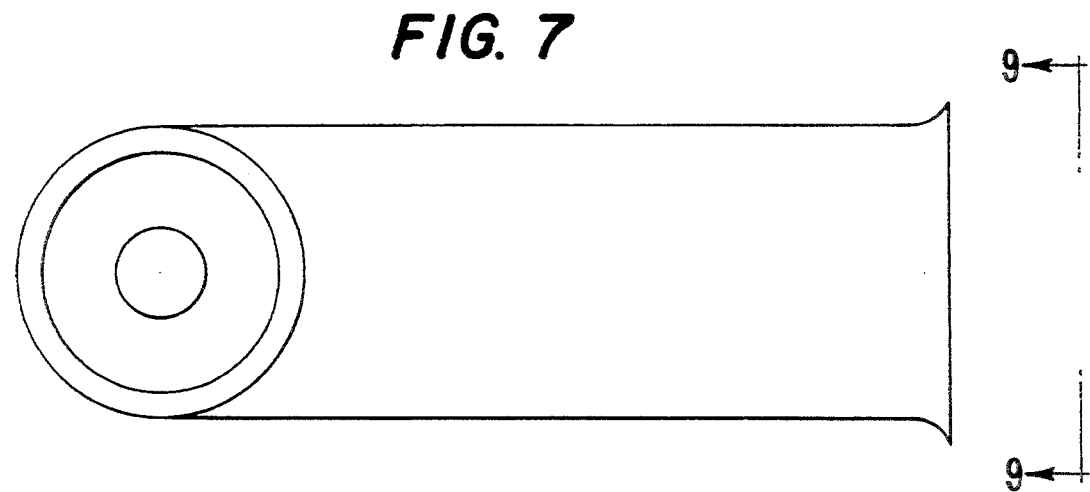
FIG. 7 is a plan view looking upwardly at the body component of FIG. 6.

With reference to FIGS. 6 and 7, it can be seen that cup end body component 14 includes an elongated barrel portion 32. And as can be seen viewing FIG. 1, end portion 26 of body component 12 is received in the open end 34 of barrel portion 32. Since end portion 26 is angularly disposed relative to axis 30 of the main body of component 12, the cup end body component 14 also is angularly disposed relative to the longitudinal axis of grip end body component 12.

It should be noted at this point that in the preferred form of the invention the body components 12 and 14 may be angularly disposed relative to one another. However, such angular disposition is not necessarily required and many of the advantages of the invention would still be provided if the body components were to be aligned on a common axis.

As can be seen from the drawings, cup end body component 14 is elongated and has a longitudinally extending axis 38. An elongated housing portion 36 is mounted at the opposite end of component 14 from open end 34. And as can be seen viewing FIG. 6, open end 34 and housing 36 are disposed in longitudinally spaced relationship along axis 38.

Figure 12:
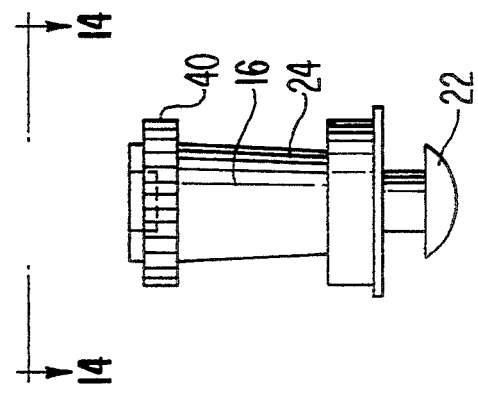
FIG. 12 is an elevational view illustrating the cup drive element of the tool of FIG. 1.

Drive element 24 is disposed within housing 36, as can be seen viewing FIG. 1. With reference to FIG. 12, it can be seen that drive element 16 includes a driven gear 40 which is coupled with shaft 24 so that driven gear 40 and shaft 24 rotate together about drive axis 42 (FIG. 1). In this connection, it can be seen that the shaft 24 of element 16 extends along axis 42 and that the button 22 is carried at the outboard end of shaft 24. Thus, shaft 24 of element 16 extends laterally outwardly from cup end component 14 at the left hand end thereof (FIG. 1), and thus axis 42 of element 16 extends laterally relative to axis 38 of cup end body component 14.

Rotatable driving component 18 is drivingly coupled to the rotatable cup drive element 16 for rotating the latter about axis 42. The rotatable driving component 18 is illustrated in detail in FIGS. 11 and 13 and includes an elongated, rotatable, flexible driving shaft 44 which extends longitudinally of rotatable driving component 18. When the tool 10 is assembled as shown in FIG. 1, shaft 44 is flexed slightly so that it extends longitudinally of both the grip end body component 12 and the cup end body component 14. Shaft 44 also therefore extends longitudinally of both axis 30 and axis 38.

Rotatable driving component 18 also includes an enlarged shaft portion 46 and a driving gear 48 mounted at the outboard end of enlarged shaft portion 46. Thus, driving gear 48 is coupled with driving shaft 18 for rotation therewith about the axis of the latter.

Shaft 44 is provided with a length 45 of reduced diameter adjacent portion 46. For example, in the embodiment illustrated in FIG. 11, length 45 has a diameter which is approximately ⅜ of the diameter of the remainder of shaft 44. Moreover, in the embodiment of FIG. 11, length 45 has a length of about 0.219" as compared to an overall length of about 1.542" for the entirety of shaft 44. As can be seen viewing FIG. 1, length 45 is positioned at the point where shaft 44 flexes to the greatest extent during operation to thereby relieve stresses on the shaft and permit the shaft 44 and enlarged portion 46 to turn freely within body components 12 and 16. In particular, the length and diameter of length 45 should be selected so that the tensile stresses imposed on the stretched side thereof during operation do not substantially exceed the tensile strength of the plastic material from which the shaft is formed.

With reference to FIGS. 1 and 6, it can be seen that housing 36 includes a centering pin 49 which is disposed on axis 42. A corresponding hole 50 is provided in the end of shaft 24. Thus, centering pin 49 is received in hole 50 to maintain drive element 16 in a proper rotating position when the device is assembled as shown in FIG. 1.

Gears 40 and 48 are intermeshed for rotation together when the device is fully assembled as shown in FIG. 1. And in this regard, it should be noted that gear 48 is a conventional drive gear whereas gear 40 is a pinion gear disposed for rotation about axis 42. Axes 38 and 42 are preferably disposed at an angle of approximately 90° relative to one another. In this connection, it should be appreciated that gears 40 and 48 are configured and arranged so as to maintain drive element 16 in its operating position when gears 40 and 48 are intermeshed. Thus, it should be noted, with reference to FIG. 1, that drive gear 48 is positioned beneath the teeth of driven pinion gear 40 so that the downward movement of element 16 is physically impeded by the positioning of the gears.

It should also be noted that end portion 26 of grip end body component 12 has an end surface 52 (FIG. 8) disposed in a plane which is generally perpendicular relative to axis 38. Also, driving component 18 has a corresponding, parallel surface 54 located at the inboard end 46a of enlarged shaft portion 46. As can be seen in FIG. 1, the surfaces 52 and 54 are in close proximity to one another so as to present interengageable shaft positioning structure for preventing the driving component 18 from moving out of its operating position when the device is assembled as shown in FIG. 1. Thus, to assembly tool 10, element 16 is inserted into housing 36, component 18 is inserted into body component 14, and then portion 26 of the component 12 is inserted into end 34 to bring the surfaces 52 and 54 into close proximity.

With further reference to FIG. 1, it can be seen that shaft 44 is grasped by the chuck 56 of a conventional dental drive system. Such drive systems are well known and conventionally used and the drive system forms no part of the present invention. Suffice it to say that end portion 28 of grip end component 12 is cylindrically shaped and provides an opening designed to receive the chuck components of the drive system as shown. Thus, the shaft 44 may be rotated by the drive system so as to rapidly rotate component 18, element 16 and button 22, to thus rotate cup 20 so as to perform teeth cleaning and polishing operations.

Figure 9:
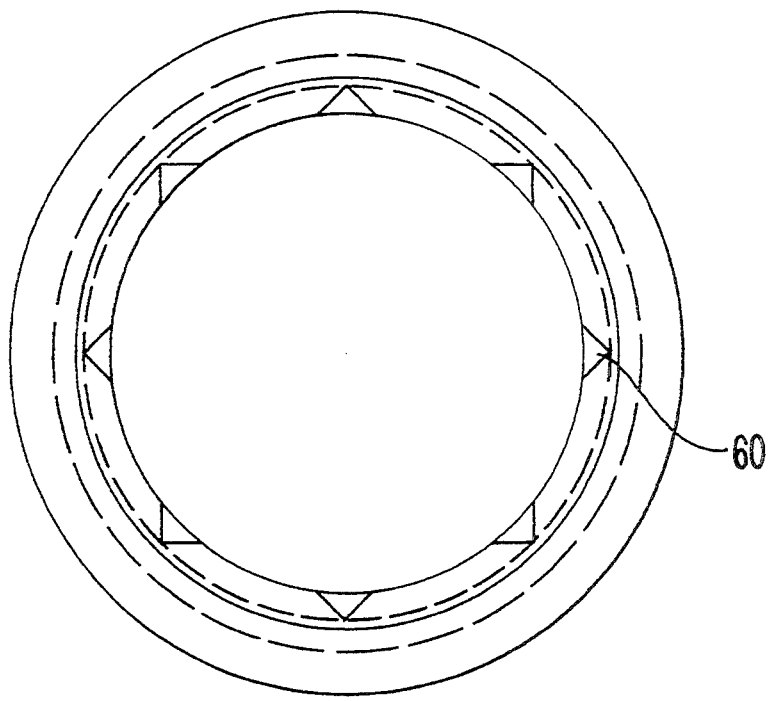
FIG. 9 is a right hand end view taken along the line 9—9 of FIG. 7.
Figure 10:
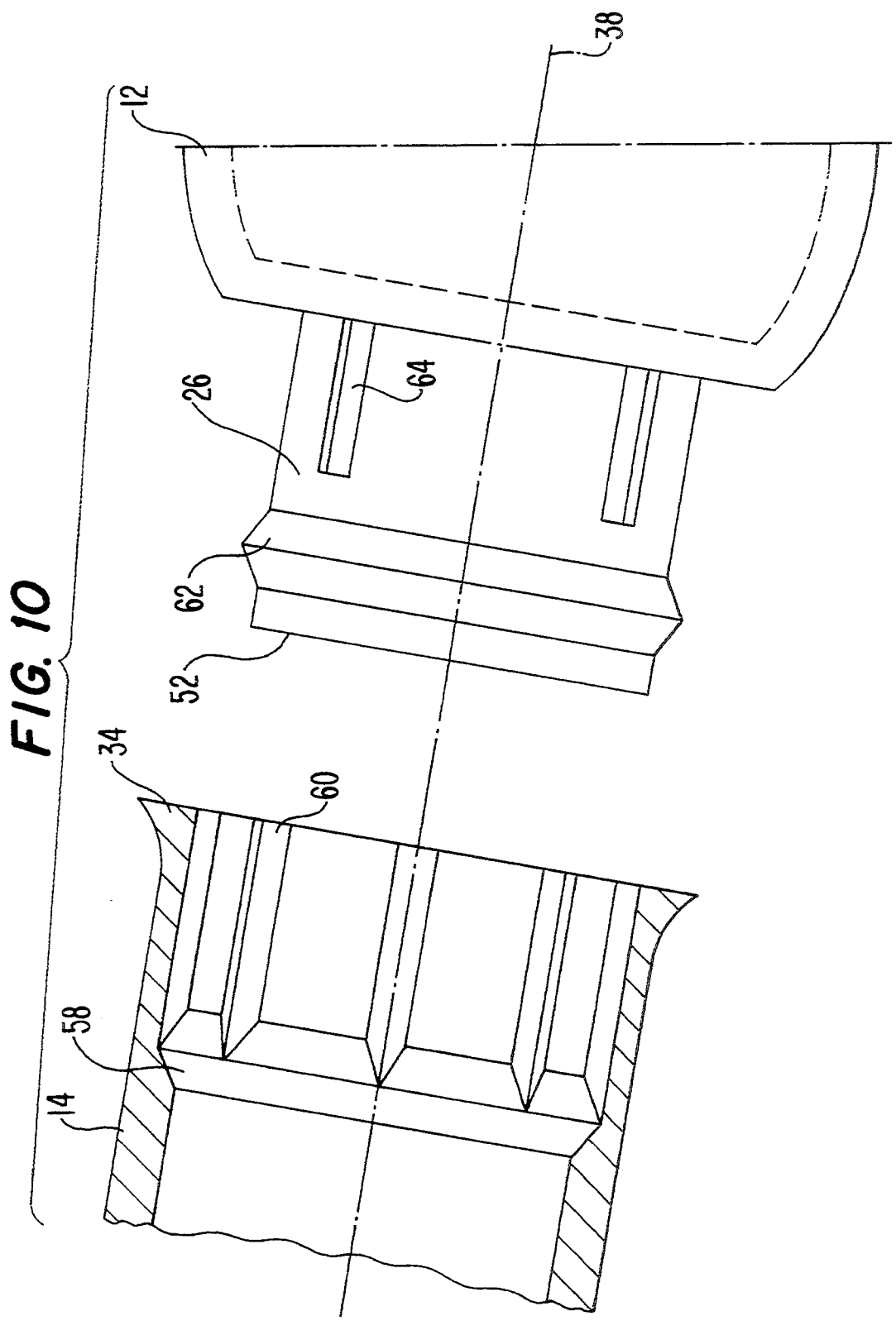
FIG. 10 is an enlarged detail view, partially in cross-section, illustrating the structure for holding the components of the tool of FIG. 1 together in accordance with the invention.

FIG. 10 includes a cross-sectional view of end 34 of cup end body component 14. FIG. 10 also includes an external view of end portion 26 of grip end body component 12. As can be seen in FIG. 10, component 14 is provided with an annular groove 58 which is concentric with axis 38 and extends therearound in a plane which is substantially perpendicular to axis 38. Component 14 also is provided with a series of elongated notches 60 which extend longitudinally of component 14 in general parallelism relative to axis 38. As can be seen in FIG. 9, the notches 60 each may have a V-shaped cross-sectional configuration. And as can be seen from FIG. 10, groove 58 also may have a generally V-shaped cross-sectional configuration.

Body component 12 is provided with an annular rib 62 which is concentric with and extends around axis 38. Rib 62 is disposed generally in a plane which is perpendicular to axis 38. Component 12 is also provided with a series of elongated ridges 64 shown in FIG. 10. The ridges 64 extend longitudinally of component 12 in general parallelism relative to axis 38. As shown in FIG. 10, rib 62 may have a triangular cross-sectional configuration which has a complementary shape relative to the V-shaped configuration of groove 58. And with reference to FIG. 8, it can be seen that the ridges 64 may have a triangular cross-sectional configuration which is complementary relative to the V-shaped configuration of notches 60.

Preferably, the various components of the tool 10 other than the cup 20 may each be formed by injection molding of a thermoplastic material. Ideally, body components 12 and 14, cup drive element 16 and driving component 18 each comprises an injection molded plastic monolith. In particular, components 12 and 14 may preferably be formed from a 50-50 wt % mixture of Minlon 10B40 (duPont) and nylon 101 (duPont), whereas rotatable cup drive element 16 and rotatable driving component 18 may preferably be formed from Delrin 500 (duPont), an acetal homopolymer. Thus, the various components feature durability, heat dissipation and gear compatibility. Moreover, the resin materials utilized for forming components 12 and 14 provide sufficient resiliency to permit insertion of end portion 26 into the open end 34 of component 14. Thus, open end 34 flexes outwardly until annular rib 62 snaps into groove 58 and ridges 64 snap into corresponding notches 60. Groove 58 and rib 62 thus provide axial locking structure holding components 12 and 14 together so as to prevent relative axial movement of components 14 and 12 along axis 38. On the other hand, annular groove 58 and annular rib 62 provide structure facilitating 360° relative rotation of component 14 about axis 38 relative to component 12. Notches 60 and ridges 64 provide releasable angular locking structure selectively inhibiting relative rotation of body components 12 and 14. If it is desired to rotate body component 14 relative to body component 12, it is necessary to exert sufficient twisting force on body component 14 to flex open end 34 outwardly and force ridges 64 out of notches 60 and to continue twisting component 14 until the next notch 60 is encountered. At this point the ridge 64 will snap into the new notch 60 for once again holding component 14 in a desired angular position relative to component 12.

Returning now to FIG. 1, it can be seen that axes and 38 preferably cross one another. It should also be noted at this point that axis 38 should preferably be inclined at an angle α of about 8 to 120 relative to axis 30. More preferably, angle α should be about 10°. Accordingly, since axis 30 and 38 are disposed in a non-parallel relationship, and since body component 14 is fully rotatable for 360° about axis 38 relative to body component 12, maximum maneuverability and flexibility is provided to facilitate accessibility to hard-to-reach areas. Thus, the device of the present invention allows the user to clean and polish teeth faster, easier and more thoroughly than ever before. And because the device of the present invention is inexpensive and disposable, cross-contamination is prevented and there is no need for the time-consuming cleaning, lubricating and sterilizing procedures normally associated with prior art dental prophy tools.

We claim:

1. An adjustable, disposable dental prophy tool comprising:

an elongated grip end body component having first and second longitudinally spaced opposite ends;

an elongated cup end body component having a longitudinally extending axis and third and fourth longitudinally spaced opposite ends, said third end of the cup end body component being mounted on the grip end body component at the second end of the latter, said cup end body component being fully rotatable for 360° about said axis thereof relative to said grip end body component;

a cup drive element extending laterally outwardly from the fourth end of the cup end body component, said cup drive element being mounted at said fourth end for rotation about a drive axis which extends laterally of said longitudinally extending axis; and a rotatable driving component which is drivingly connected to said cup drive element for rotating the latter about said drive axis, said driving component including a plastic, moldable, elongated, rotatable, flexible driving shaft which extends longitudinally through said grip end body component and said cup end body component.

2. An adjustable, disposable dental prophy tool as set forth in claim 1, wherein said cup drive element includes a driven gear and an elongated cup drive shaft extending along said drive axis, said driven gear and said cup drive shaft being coupled for rotation together about said drive axis, said driving component including a driving gear coupled with said driving shaft for rotation therewith about the axis of the driving shaft, said gears being intermeshed for rotation together.

3. An adjustable, disposable dental prophy tool as set forth in claim 1, wherein said tool includes axial locking structure at said third end of the cup end body component and said second end of the grip end body component holding said body components together to prevent relative axial movement thereof in a direction along said longitudinally extending axis and facilitate said 360° relative rotation thereof.

4. An adjustable, disposable dental prophy tool as set forth in claim 3, wherein said tool includes releasable angular locking structure at said third end of the cup end body component and said second end of the grip end body component selectively inhibiting said relative rotation.

5. An adjustable, disposable dental prophy tool as set forth in claim 1, wherein said tool includes releasable angular locking structure at said third end of the cup end body component and said second end of the grip end body component selectively inhibiting said relative rotation.

6. An adjustable disposable dental prophy tool as set forth in claim 5, wherein said angular locking structure includes an elongated notch in one of said components and a complementary mating elongated ridge carried by the other of said components, said notch and said ridge each extending in parallelism to said longitudinally extending axis, said notch and said ridge cooperating to inhibit said relative rotation when the ridge is disposed in the notch.

7. An adjustable, disposable dental prophy tool as set forth in claim 1, wherein said gears are configured so as to hold said cup drive element in its operating disposition when the gears are intermeshed.

8. An adjustable, disposable dental prophy tool as set forth in claim 1, wherein said cup end body component includes an elongated barrel portion and an elongated drive element housing portion extending laterally of said barrel portion, said drive element being mounted within said housing portion.

9. An adjustable, disposable dental prophy tool as set forth in claim 1, wherein said body components and said drive element each comprises an injection molded plastic monolith.

10. An adjustable, disposable dental prophy tool as set forth in claim 1, wherein said body components, said driving component and said drive element each comprises an injection molded plastic monolith.

11. An adjustable, disposable dental prophy tool comprising:

an elongated grip end body component having first and second longitudinally spaced opposite ends;

an elongated cup end body component having a longitudinally extending axis and third and fourth longitudinally spaced opposite ends, said third end of the cup end body component being mounted on the grip end body component at the second end of the latter, said cup end body component being fully rotatable for 360° about said axis thereof relative to said grip end body component;

a cup drive element extending laterally outwardly from the fourth end of the cup end body component, said cup drive element being mounted at said fourth end for rotation about a drive axis which extends laterally of said longitudinally extending axis; and axial locking structure at said third end of the cup end body component and said second end of the grip end body component holding said body components together to prevent relative axial movement thereof in a direction along said longitudinally extending axis and facilitate said 360° relative rotation thereof, said axial locking structure including an annular groove in one of said components and a complementary mating annular rib carried by the other of said components, said rib being disposed in said groove, said rib and said groove being disposed in a common plane and each being concentric with said longitudinally extending axis.

12. An adjustable, disposable dental prophy tool comprising:

an elongated grip end body component having first and second longitudinally spaced opposite ends;

an elongated cup end body component having a longitudinally extending axis and third and fourth longitudinally spaced opposite ends, said third end of the cup end body component being mounted on the grip end body component at the second end of the latter, said cup end body component being fully rotatable for 360° about said axis thereof relative to said grip end body component;

a cup drive element extending laterally outwardly from the fourth end of the cup end body component, said cup drive element being mounted at said fourth end for rotation about a drive axis which extends laterally of said longitudinally extending axis;

a rotatable driving component which is drivingly connected to said cup drive element for rotating the latter about said drive axis, said driving component including an elongated, rotatable, flexible driving shaft which extends longitudinally said grip end body component and said cup end body component; and a first shaft positioning element on said grip end body component and a second shaft positioning element on said driving component, said shaft positioning elements being interengaged to maintain the driving component in its operating position when the cup end body component is mounted on the grip end body component.

13. An adjustable, disposable dental prophy tool as set forth in claim 12, wherein said gears are configured so as to hold said cup drive element in its operating disposition when the gears are intermeshed.

14. An adjustable, disposable dental prophy tool comprising:

an elongated grip end body component having a first longitudinally extending axis and first and second longitudinally spaced opposite ends;

an elongated cup end body component having a second longitudinally extending axis and third and fourth longitudinally spaced opposite ends, said third end of the cup end body component being mounted on the grip end body component at the second end of the latter, with said first and second axes disposed in a non-parallel relationship, said cup end body component being fully rotatable for 360° about said second axis thereof relative to said grip end body component;

a cup drive element extending laterally outwardly from the fourth end of the cup end body component, said cup drive element being mounted at said fourth end for rotation about a drive axis which extends laterally of said second axis; and a rotatable driving component which is drivingly connected to said cup drive element for rotating the latter about said drive axis, said driving component including a plastic; moldable, elongated, rotatable, flexible driving shaft which extends longitudinally through said grip end body component and said cup end body component along said first and second axes.

15. An adjustable, disposable dental prophy tool as set forth in claim 14, wherein said first and second axes cross one another.-

16. An adjustable, disposable dental prophy tool as set forth in claim 15, wherein said second axis is inclined at an angle of approximately 8° to 12° relative to said first axis.

17. An adjustable, disposable dental prophy tool as set forth in claim 14, wherein said cup drive element includes a driven gear and an elongated cup drive shaft extending along said drive axis, said driven gear and said cup drive shaft being coupled for rotation together about said drive axis, said driving component including a driving gear coupled with said driving shaft for rotation therewith about the axis of the driving shaft, said gears being intermeshed for rotation together.

18. An adjustable, disposable dental prophy tool as set forth in claim 14, wherein said tool includes axial locking structure at said third end of the cup end body component and said second end of the grip end body component holding said body components together to prevent relative axial movement thereof in a direction along said second axis and facilitate said 360° relative rotation thereof.

19. An adjustable, disposable dental prophy tool as set forth in claim 18, wherein said tool includes releasable angular locking structure at said third end of the cup end body component and said second end of the grip end body component selectively inhibiting said relative rotation.

20. An adjustable, disposable dental prophy tool as set forth in claim 14, wherein said tool includes releasable angular locking structure at said third end of the cup end body component and said second end of the grip end body component selectively inhibiting said relative rotation.

21. An adjustable, disposable dental prophy tool as set forth in claim 20, wherein said angular locking structure includes an elongated notch in one of said components and a complementary mating elongated ridge carried by the other of said components, said notch and said ridge each extending in parallelism to said second axis, said notch and said ridge cooperating to inhibit said relative rotation when the ridge is disposed in the notch.

22. An adjustable, disposable dental prophy tool as set forth in claim 14, wherein said gears are configured so as to hold said cup drive element in its operating disposition when the gears are intermeshed.

23. An adjustable, disposable dental prophy tool as set forth in claim 14, wherein said cup end body component includes an elongated barrel portion and an elongated drive element housing portion extending laterally of said barrel portion, said drive element being mounted within said housing portion.

24. An adjustable, disposable dental prophy tool as set forth in claim 14, wherein said body components and said drive element each comprises an injection molded plastic monolith.

25. An adjustable, disposable dental prophy tool as set forth in claim 14, wherein said body components, said driving component and said drive element each comprises an injection molded plastic monolith.

26. An adjustable, disposable dental prophy tool comprising:

an elongated grip end body component having a first longitudinally extending axis and first and second longitudinally spaced opposite ends;

an elongated cup end body component having a second longitudinally extending axis and third and fourth longitudinally spaced opposite ends, said third end of the cup end body component being mounted on the grip end body component at the second end of the latter, with said first and second axes disposed in a non-parallel relationship, said cup end body component being fully rotatable for 360° about said second axis thereof relative to said grip end body component;

a cup drive element extending laterally outwardly from the fourth end of the cup end body component, said cup drive element being mounted at said fourth end for rotation about a drive axis which extends laterally of said second axis; and axial locking structure at said third end of the cup end body component and said second end of the grip end body component holding said body components together to prevent relative axial movement thereof in a direction along said second axis and facilitate said 360° relative rotation thereof, said axial locking structure including an annular groove in one of said components and a complementary mating annular rib carried by the other of said components, said rib being disposed in said groove, said rib and said groove being disposed in a common plane and each being concentric with said second axis.

27. An adjustable, disposable dental prophy tool comprising:

an elongated grip end body component having a first longitudinally extending axis and first and second longitudinally spaced opposite ends;

an elongated cup end body component having a second longitudinally extending axis and third and fourth longitudinally spaced opposite ends, said third end of the cup end body component being mounted on the grip end body component at the second end of the latter, with said first and second axes disposed in a non-parallel relationship, said cup end body component being fully rotatable for 360° about said second axis thereof relative to said grip end body component;

a cup drive element extending laterally outwardly from the fourth end of the cup end body component, said cup drive element being mounted at said fourth end for rotation about a drive axis which extends laterally of said second axis;

a rotatable driving component which is drivingly connected to said cup drive element for rotating the latter about said drive axis, said driving component including an elongated, rotatable, flexible driving shaft which extends longitudinally of said grip end body component and said cup end body component along said first and second axes; and a first shaft positioning element on said grip end body component and a second shaft positioning element on said driving component, said shaft positioning elements being interengaged to maintain the driving component in its operating position when the cup end body component is mounted on the grip end body component.

28. An adjustable, disposable dental prophy tool as set forth in claim 27, wherein said gears are configured so as to hold said cup drive element in its operating disposition when the gears are intermeshed.

* * * * *